US008662440B2

(12) United States Patent
Journade et al.

(10) Patent No.: US 8,662,440 B2
(45) Date of Patent: *Mar. 4, 2014

(54) AFT PYLON FAIRING FOR AN AIRCRAFT ENGINE SUSPENSION SYSTEM

(75) Inventors: Frederic Journade, Toulouse (FR); Eric Renaud, Brignemont (FR); Delphine Jalbert, Seilh (FR)

(73) Assignee: Airbus Operations S.A.S., Toulouse (FR)

( * ) Notice: Subject to any disclaimer, the term of this patent is extended or adjusted under 35 U.S.C. 154(b) by 655 days.

This patent is subject to a terminal disclaimer.

(21) Appl. No.: 12/677,139

(22) PCT Filed: Sep. 17, 2008

(86) PCT No.: PCT/EP2008/062335
§ 371 (c)(1),
(2), (4) Date: Mar. 18, 2011

(87) PCT Pub. No.: WO2009/037267
PCT Pub. Date: Mar. 26, 2009

(65) Prior Publication Data
US 2011/0155847 A1    Jun. 30, 2011

(30) Foreign Application Priority Data
Sep. 20, 2007  (FR) ...................................... 07 57712

(51) Int. Cl.
*B64D 27/00*  (2006.01)
(52) U.S. Cl.
USPC ............. 244/54; 244/130; 244/131; 244/121; 244/129.1; 248/554; 248/55; 248/556; 248/557; 60/796; 60/797

(58) Field of Classification Search
USPC ......... 244/54, 130, 131, 121, 129.1; 248/554, 248/555, 556, 557; 60/796, 797
See application file for complete search history.

(56) References Cited

U.S. PATENT DOCUMENTS

| 4,466,587 | A | * | 8/1984 | Dusa et al. ..................... 244/121 |
| 4,712,750 | A | * | 12/1987 | Ridgwell .................. 244/117 A |
| 5,524,846 | A | * | 6/1996 | Shine et al. ................. 244/53 R |
| 5,906,097 | A | * | 5/1999 | Hebert et al. ................ 60/226.1 |
| 8,118,252 | B2 | * | 2/2012 | Dumont et al. ................. 244/54 |
| 2003/0201366 | A1 | * | 10/2003 | Connelly et al. ............. 244/121 |

OTHER PUBLICATIONS

U.S. Appl. No. 12/918,500, filed Aug. 20, 2010, Journade, et al.
U.S. Appl. No. 12/918,334, filed Aug. 19, 2010, Journade, et al.
U.S. Appl. No. 12/918,530, filed Aug. 20, 2010, Journade, et al.

* cited by examiner

*Primary Examiner* — Isam Alsomiri
*Assistant Examiner* — Assres H Woldemaryam
(74) *Attorney, Agent, or Firm* — Oblon, Spivak, McClelland, Maier & Neustadt, L.L.P.

(57) ABSTRACT

This invention relates to an aft pylon fairing (30) for a suspension system of an aircraft engine, comprising two side panels (44) assembled to each other by inner cross stiffening ribs (46) spaced at intervals from each other along a longitudinal direction (X) of the fairing, and also comprising a heat protection deck (32) designed to delimit an engine core flow (36). According to the invention, it also comprises two longitudinal connecting walls (58) offsetting the deck (32) from the ribs (46), each of these two longitudinal walls (58) being provided with a first side end (62) fixed to one or the other of the two side ends (60, 60) of the deck (32), and a second side end (64) rigidly fixed to the ribs (46).

10 Claims, 3 Drawing Sheets

AFT PYLON FAIRING FOR AN AIRCRAFT ENGINE SUSPENSION SYSTEM

TECHNICAL DOMAIN

This invention relates to an aft pylon fairing for an engine suspension system designed to be inserted between an aircraft wing and the engine concerned.

The invention may be used on any type of aircraft fitted with turbojets or turboprops.

This type of suspension system, also called an <<EMS>> (Engine Mounting Structure), can be used to suspend a turbo-engine below the aircraft wing, or to mount this turbojet above this wing.

STATE OF PRIOR ART

Such a suspension system is designed to form the connecting interface between a turbo-engine and a wing of the aircraft. It transmits forces generated by the associated turbo-engine to the aircraft structure, and also is used to route fuel, electrical and hydraulic and air systems between the engine and the aircraft.

The suspension system comprises a rigid structure also called the primary structure, often a <<box>> type structure, in other words formed by the assembly of lower and upper spars and side panels connected to each other by cross stiffening ribs, in order to transmit forces.

The system is also provided with suspension means inserted between the turbo-engine and the rigid structure, these means globally comprising two engine suspensions, and a system for resisting thrusts generated by the turbo-engine. In prior art, this force resistance system normally comprises two side connecting rods connected firstly to an aft part of the turbojet fan casing, and secondly to an aft attachment fixed onto the central part of the turbojet.

In the same way, the suspension system also comprises another series of attachments forming a suspension system inserted between the rigid structure and the aircraft wing, this system normally being composed of two or three attachments.

Moreover, the pylon is provided with a plurality of secondary structures segregating and maintaining the systems while supporting pylon fairing elements, which are usually in the form of assemblies of panels added onto the structures. As is well known to those skilled in the art, secondary structures are differentiated from the rigid structure by the fact that they are not designed to transfer forces from the engine to be transmitted to the aircraft wing.

The secondary structures include the aft pylon fairing (APF) that has a plurality of functions including the formation of a thermal or fire resistant barrier, and the formation of aerodynamic continuity between the engine exhaust and the suspension pylon.

The aft pylon fairing is usually in the form of a box comprising two side panels assembled to each other by inner cross stiffening ribs spaced at intervals from each other along a longitudinal direction of the fairing, and a heat protection deck. Note that this box is usually not closed opposite the heat protection deck, in other words in the upper part when the engine will be suspended under the aircraft wing, considering that this is the location at which it is connected to the other pylon structures.

The heat protection deck is provided with an outer surface designed to delimit the engine core flow which is delimited by this deck, while the engine fan flow is delimited by the outer surfaces of the side panels, due to their location in the annular fan flow duct of the engine, and/or at the engine exhaust.

In solutions according to prior art, the heat protection deck is mounted fixed on the box inner cross ribs with which it is in contact, and its opposite side ends are mounted fixed on the two side panels that also match the cross ribs.

In this configuration the heat protection deck is in contact with the very hot core engine flow, which means that it deforms strongly due to thermal expansion. However, its corresponding embedments into the inner cross ribs and into the lower end of each of the two side panels create high thermomechanical stresses within the deck and the side panels, which is obviously not good for these elements.

Note that this phenomenon through which high thermomechanical stresses are introduced due to the large thermal expansion of the deck is accentuated by the fact that the side panels are immersed in the fairly cool fan flow, such that their deformation caused by thermal expansion is very small. Nevertheless, they are affected by significant deformation caused by the stresses set up resulting from the expansion of the deck to which they are directly and rigidly connected, which degrades their aerodynamic shape and more generally deteriorates the global aerodynamic quality of the fairing. Naturally, such degradation increases the generated parasite drag.

Consequently, note that the aerodynamic quality of the fairing is also degraded by local deformations of the heat protection deck which cannot expand freely unstressed, because it is built into specific fairing elements such as the inner ribs, as described above. Since the core engine flow is a very fast jet, local deformations encountered at the deck create a fairly large parasite drag.

Finally, note that the fairly cool fan flow does not directly follow the surface of the inner cross ribs due to their location inside the box, and the ribs may be sensitive to heat transferred from the heat protection deck with which they are in contact. Thus, to enable these ribs to perform their function to mechanically support the different elements of the box shaped fairing, it may be necessary to oversize them and/or to use expensive materials with good heat resistance properties to manufacture them.

SUMMARY OF THE INVENTION

Therefore, the purpose of the invention is to at least partially correct the disadvantages mentioned above relative to embodiments according to prior art.

To achieve this, the object of the invention is an aft pylon fairing for an engine suspension system that will be inserted between an aircraft wing and the engine, the fairing forming a box comprising two side panels assembled together by inner cross stiffening ribs at a spacing from each other along a longitudinal direction of the fairing, and also comprising a heat protection deck provided with an outer surface that will delimit a core engine flow, the heat protection deck being provided with two opposite side ends.

According to the invention, the fairing also comprises two longitudinal connecting walls offsetting the heat protection deck from the inner cross stiffening ribs, these two longitudinal walls each being provided with a first side end fixed to one or the other of the two side ends of the heat protection deck, and a second side end rigidly fixed to the inner cross stiffening ribs.

One of the specific features of this invention is the fact that this deck is now offset from the inner cross ribs by means of longitudinal walls, it being understood that these are the same walls that indirectly (and preferably alone) are used for assembly of the deck onto the ribs. In other words, the deck is no longer mounted on the ribs directly, which advantageously allows the deck to deform more freely due to thermal expansion following the large amount of heat released by the core engine flow delimited by this deck.

This innovative configuration in which the deck is relatively free to expand relative to the inner ribs considerably reduces the thermomechanical stresses applied to the deck as a result of such an expansion, below the values of stresses found in prior embodiments in which the main mechanism by which thermomechanical stresses are introduced into the deck is the fact that the deck is built into the ribs.

In this respect, considering that the deck is capable of deforming by thermal expansion since it is less stressed than before, local deformations degrading the aerodynamic quality of this deck are also significantly reduced. Therefore, the result is an improvement in the global aerodynamic quality of the fairing, significantly reducing parasite drag effects and thereby improving the performance/consumption ratio of the aircraft.

Furthermore, all the advantages mentioned above are accentuated by the fact that the rigid direct mechanical link between the deck and the side panels is also preferably eliminated, to create a mechanical break extending longitudinally between these elements, therefore the deck is capable of expanding without taking the side panels with it.

Preferably, the deck offset from the inner ribs has no contact with these ribs, such that heat transmitted to these ribs through the deck passes firstly through the longitudinal walls. This means that the intensity of the heat is reduced before it reaches the inner ribs which are therefore only slightly heated, in particular making it advantageously possible to use materials other than expensive materials with good heat resistance properties, but without necessarily oversizing these ribs.

Furthermore, since thermal expansion of the deck takes place fairly freely relative to the ribs and side panels, the induced deformed shape of these ribs and panels is significantly reduced so that the aft pylon fairing can be integrated into the other secondary structures of the pylon, like the aft structure.

Finally, note that the presence of longitudinal walls releases the thermal expansion of the deck, which has the effect of reducing mechanical stresses in the deck. This specific feature, plus the different advantageous technical effects mentioned above, makes it possible to envisage reducing the thickness of the deck below thicknesses used in prior art, which in particularly results in mass and cost savings.

Preferably, the first end of each longitudinal wall in any arbitrary cross-section of the fairing, together with its associated heat protection deck side end work together to form a tip, preferably in a Y-shape. In other words, each longitudinal wall is such that its first side end is in firm contact with its associated deck side end, before progressively moving away from this deck towards its second side end directly added onto and fixed to the inner ribs.

This preferred tip shape advantageously makes it possible to maintain an effective separation between the core engine flow circulating under the deck and the fan flow delimited by the side panels, such that the side panels are no longer exposed to the high temperatures of the core engine flow.

Preferably, still in any arbitrary cross-section of the fairing, every longitudinal wall is approximately in the form of a straight line, and the heat protection deck is approximately in the form of a curved line opening outwards relative to the fairing, this shape being perfectly adapted to give good aerodynamic flow of the core engine flow.

The heat protection deck is made in a single piece, once again to minimise aerodynamic disturbances and the parasite drag created by them.

Similarly and preferably, each of the two longitudinal walls is made so as to form a single piece.

In this respect, note that each of the two longitudinal walls and the deck extend over a very long length of the fairing, preferably as far as the beginning of its aft aerodynamic pyramid, or leading edge.

Also preferably, each of the two longitudinal walls and the heat protection deck are made of aluminum or a composite material formed by a mix of resin and carbon and/or glass fibres, which results in mass and cost savings. Nevertheless, it is even more preferable if they are made of titanium.

Preferably, the second side end of each of these two longitudinal walls is mounted fixed on a lower portion of the inner stiffening cross ribs, at a distance from the side panels that are preferably mounted fixed on side portions of these inner cross ribs.

More generally and as mentioned above, the heat protection deck and the two longitudinal walls do not have any rigid direct mechanical link with the fairing side panels, which means that these fairing side panels are only added on and fixed indirectly to the heat protection deck and the two longitudinal walls, actually through inner cross ribs. In other words, there is a longitudinal mechanical break between the deck and each of the side panels.

In this configuration, the deck is practically free from the side panels, which even further reduces thermomechanical stresses applied to the deck due to its deformation caused by thermal expansion.

Once again, the aerodynamic quality of this deck is considerably increased considering that the deck is capable of deforming by thermal expansion with lower constraints than before.

It is even further increased because the lack of embedment of the deck into the side panels advantageously prevents these side panels from being stressed and deformed, which could occur following deformation of the deck due to thermal expansion. In this respect, note that the side panels are immersed in the fairly cool fan flow, such that they experience very little deformation due to thermal expansion. Thus, their global deformation level is kept relatively low, which induces a very satisfactory aerodynamic quality participating in reducing parasite drag effects and improving the performance/consumption ratio of the aircraft.

Preferably, each of the two side panels is made so as to form a single piece.

Similarly, each of the two side panels is preferably made of aluminum or a composite material formed by a mix of resin and carbon and/or glass fibres, or even titanium.

According to one preferred embodiment of this invention, the fairing also comprises two aerodynamic extensions of the side panels, each associated with one of the side panels that it extends toward the heat protection deck, each aerodynamic extension having a first end rigidly added onto its associated side panel, and a second end cooperating with one of the side ends of the heat protection deck with which it is in bearing contact.

Thus, there is no rigid link between the aerodynamic extension and the deck, such that the deck can continue to deform freely by expansion. Naturally, it would have been possible to envisage an alternative solution in which each side panel extends beyond the inner cross ribs until its end cooperates with one of the heat protection deck side ends with which it would always be in bearing contact, and not directly and rigidly connected to it.

Preferably, each of the two aerodynamic extensions is made so that it forms a single piece, for example made of aluminum or a composite material formed by a mix of resin and carbon and/or glass fibres, or even titanium.

Another purpose of the invention is an engine suspension system that will be inserted between an aircraft wing and the engine, this system comprising an aft pylon fairing like that described above.

Another purpose of the invention is an engine assembly comprising an engine such as a turbojet and a suspension system for this engine, this system complying with what has just been described.

Finally, another purpose of this invention is an aircraft comprising at least one such engine assembly.

Other advantages and characteristics of the invention will become clear in the non-limitative detailed description given below.

BRIEF DESCRIPTION OF THE DRAWINGS

This description will be made with reference to attached drawings among which.

DETAILED DESCRIPTION OF DIFFERENT PREFERRED EMBODIMENTS

Figure 1:
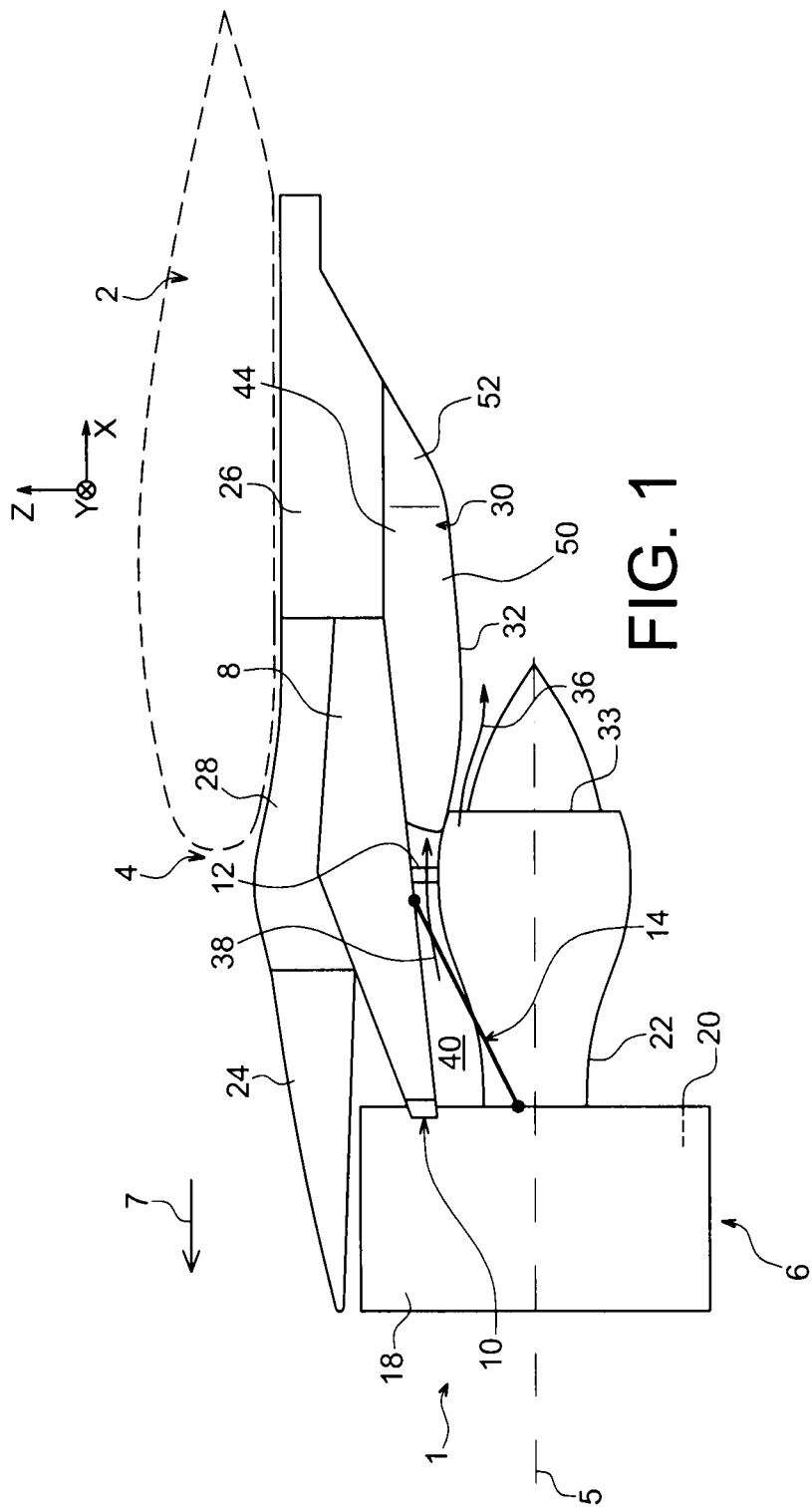
FIG. 1 represents a diagrammatic side view of an engine assembly for an aircraft, comprising a suspension system according to a preferred embodiment of this invention.

FIG. 1 shows an aircraft engine assembly to be fixed under a wing 2 of this aircraft, this assembly comprising a suspension system 4 according to a preferred embodiment of this invention, and an engine 6 such as a turbojet suspended under this system 4.

Globally, the suspension system 4 comprises a rigid structure 8, also called the primary structure, carrying the suspension means for the engine 6, these suspension means being provided with several engine suspensions 10, 12, and a system 14 for resisting thrusts generated by the engine 6.

Note that the assembly 1 will be surrounded by a nacelle (not shown) and that the suspension system 4 comprises another series of suspensions (not shown) added onto the rigid structure 8 and that suspend this assembly 1 under the aircraft wing 2.

Throughout the following description, by convention, X is the longitudinal direction of the system 4 and is also effectively the longitudinal direction of the turbojet 6 and the aft pylon fairing that will be presented below, this X direction being parallel to a longitudinal axis 5 of this turbojet 6. The Y direction is oriented in the direction transverse to the system 4 and is also effectively the direction transverse to the turbojet 6 and to the aft pylon fairing, while Z is the vertical direction or the height, these three directions X, Y and Z being orthogonal to each other.

Furthermore, the terms <<forward>> and <<aft>> should be considered relative to a direction of movement of the aircraft developed as a result of the thrust applied by the turbojet 6, this direction being shown diagrammatically by the arrow 7.

Therefore, FIG. 1 includes the two engine suspensions 10, 12, the thrust resistance system 14, the rigid structure 8 of the suspension system 4 and a plurality of secondary structures added onto the rigid structure 8. These secondary structures segregating and maintaining the systems while supporting pylon fairing elements will be described below.

Note that the turbojet 6 is provided with a large fan casing 18 at its forward end delimiting an annular fan duct 20, and with a smaller central casing 22 at its aft end, enclosing the core of this turbojet. The casings 18 and 22 are obviously rigidly fixed to each other.

As can be seen in FIG. 1, there are two of the engine suspensions 10, 12 for the system 4, and they are called the forward engine suspension and the aft engine suspension respectively.

In this preferred embodiment of this invention, the rigid structure 8 is in the form of a box extending from the aft part towards the forward end, approximately along the X direction.

The box 8 is then in the form of a pylon with a design similar to that usually observed for turbojet suspension pylons, particularly in that it is provided with cross ribs (not shown) each in the form of a rectangle oriented in a YZ plane.

The suspension means of this preferred embodiment comprise firstly the forward engine suspension 10 inserted between a forward end of the rigid structure 8 also called the pyramid, and an upper part of the fan casing 18. The forward engine suspension 10 is designed conventionally in a manner known to those skilled in the art.

Secondly, the aft engine suspension 12, also made in a conventional manner known to those skilled in the art, is inserted between the rigid structure 8 and the central casing 22.

Also with reference to FIG. 1, the secondary structures of the pylon 4 include a forward aerodynamic structure 24, an aft aerodynamic structure 26, a connection fairing 28 for the forward and aft aerodynamic structures, and an aft pylon fairing 30.

Globally, these secondary structures are conventional elements identical to or similar to those encountered in prior art and known to those skilled in the art, except for the aft pylon fairing 30 that will be described in detail below.

More precisely, the forward aerodynamic structure 24 is placed in the lower forward extension of the wing 2 and above the primary structure 8. It is mounted fixed onto the rigid structure 8 and it forms an aerodynamic profile between an upper part of the fan covers hinged on this part, and the leading edge of the wing. This forward aerodynamic structure 24 then not only forms a pylon fairing, but is also used for placement, segregation and routing of the different systems (air, electrical, hydraulic, fuel). Furthermore, since the forward part of this structure 24 is not in contact with the rigid structure 8, a heat exchanger is usually inserted in the space defined between these two elements.

The connection fairing 28, also called the <<karman>>, is located directly in the aft prolongation of this structure 24, and still under the wing and mounted above the rigid structure 8. Then, further towards the aft direction, the connection fairing 28 is prolonged by the aft aerodynamic structure 26 that contains part of the pylon equipment. This structure 26 is preferably located aft from the rigid structure 8, and is therefore suspended under the aircraft wing.

Finally, the aft pylon fairing 30, or "shield", is located under the rigid structure 8 and the aft aerodynamic structure 26. It essentially forms a heat barrier also called a fire barrier that protects the pylon and the wing from heat dissipated by the core engine flow, and aerodynamic continuity between the engine exhaust and the suspension pylon.

In a manner known to those skilled in the art, the fairing 30 mentioned above comprises a heat protection deck 32 provided with an outer surface that will delimit the core engine flow from the engine that the deck partially delimits radially outwards, this core engine flow output from the engine nozzle 33 being shown diagrammatically by the arrow 36. Furthermore, the fairing 30 also comprises two side panels 44 with outer surfaces that delimit the fan flow from the engine shown diagrammatically by the arrow 38, due to their location in the annular fan duct 40 of the engine, and/or at the engine exhaust.

Note that in the preferred embodiment described in which the engine 6 will be suspended under the aircraft wing, the heat protection deck 32 protecting the pylon and the wing from the core engine flow 36 forms a lower portion of the fairing 30. Naturally, this deck would form an upper portion of the fairing in the alternate case in which the engine is designed to be mounted above the wing.

Finally, as can be seen in FIG. 1, the forward end of the deck 32 matches the upper aft end of the nozzle 33, or is very close to this aft end of nozzle 33.

Now with reference to FIGS. 2 to 5, the figures show the aft pylon fairing 30 in more detail, which is in the general shape of a box open at the top, in other words facing the other structures of the pylon on which it will be mounted, namely the aft aerodynamic structure 26 and the rigid structure 8. The fairing 30 preferably has a plane of symmetry P corresponding to an XZ plane, this plane P also forming a vertical plane of symmetry for the entire suspension system 4, and for the engine 6.

Figure 2:
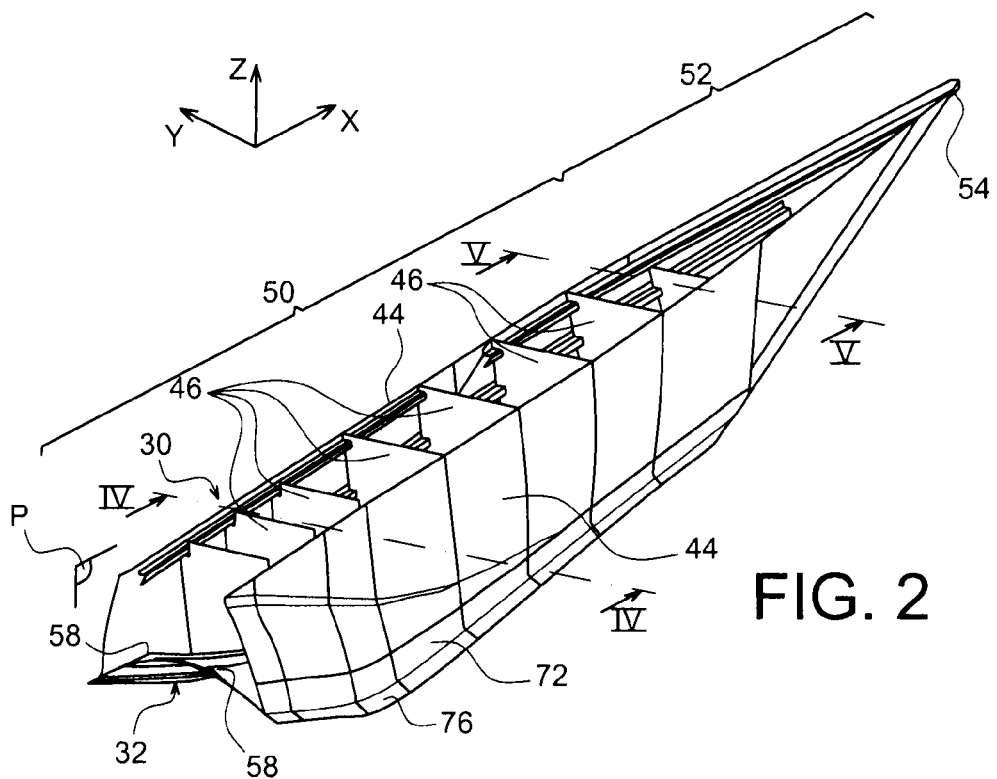
FIG. 2 shows a partial perspective view of the aft pylon fairing used on the suspension system shown in FIG. 1, this fairing also being a purpose of this invention.

With reference more particularly to FIG. 2, the box-shaped aft pylon fairing 30 comprises the two side panels 44 each approximately oriented in an XZ plane on each side of the plane P. They are assembled to each other by inner cross stiffening ribs 46 at intervals from each other along the X direction, each of these ribs 46 being oriented along a YZ plane and for example being in the form of a rectangle or a square. In this respect, although it has not been shown, the fairing 30 also preferably comprises a forward closing rib of the box.

The side panels 44 are directly mounted fixed on the side portions of each of the inner ribs 46, by conventional means known to those skilled in the art.

Furthermore, the fairing 30 includes the heat protection deck 32 in the lower part of the box, the upper part preferably remaining open before being added onto the suspension system, as can clearly be shown in FIG. 2.

Still in this figure, it can be seen that the fairing 30 is broken down into two distinct portions fixed to each other, namely a forward portion 50 forming the major part of the fairing, for example 60 to 85% of the fairing along X direction, and a small aft portion 52 globally in the form of a pyramid or a tip, the base of which is rigidly connected to the forward portion 50, and the vertex 54 of which forms an aft end of the fairing 30. For guidance, the forward portion 50 has a fairly uniform cross-section along its entire length.

The side panels 44 extend preferably each in a single piece from one end of the fairing 30 to the other, in other words both along the forward portion 50 and along the aft portion 52. On the other hand, the heat protection deck 32 preferably extends in a single piece only along the forward portion 50, and not along the aft portion 52, although this could obviously be envisaged without going outside the framework of the invention. This special feature is explained particularly by the fact that the pyramid-shaped aft portion 52 progressively moves away from the centreline of the engine, such that the core engine flow that in any case loses some of its heat intensity as it moves in the aft direction, has less effect on the temperature of the lower closing element of the pyramid 52.

Note also that the fact that each of the elements mentioned above is made from a single piece does not prevent these parts from being manufactured from several distinct portions rigidly fixed to each other, for example several subsequent portions along the X direction. This is also true for the following elements that will be described as possibly being made in a single piece.

One of the special features of this invention lies in the fact that the deck 32 is shifted downwards from the inner cross ribs 46, using two longitudinal connection walls 58 rigidly and directly added onto side ends of this deck 32 as will now be described in detail with reference to FIGS. 3 to 5.

Figure 3:
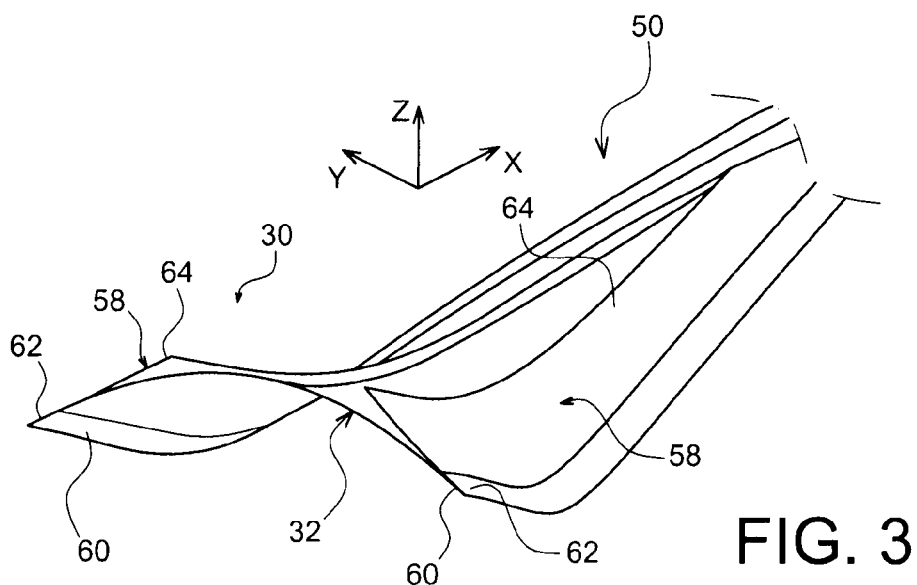
FIG. 3 shows a perspective view of a lower part of the aft pylon fairing shown in FIG. 2, including the heat protection deck and its associated longitudinal connection walls.

FIG. 3 shows that each longitudinal wall 58 has a first lower side end 62, which is rigidly and directly fixed onto one of the side ends 60 of the deck 32, for example by riveting or similar means.

Thus, it is preferable that each of the two rigid and direct mechanical junctions between the two ends 60 and 62 is made along the entire length of the forward portion 50 of the fairing, approximately along the X direction.

Figure 4:
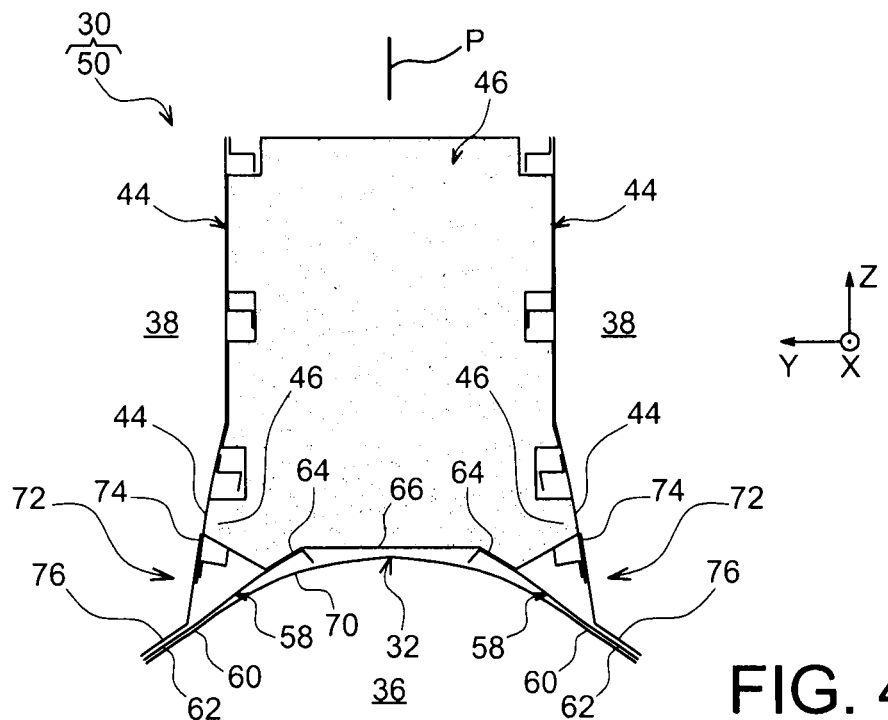
FIG. 4 shows a cross-sectional view taken along line IV-IV in FIG. 2.

Each of the two longitudinal walls 58 that extend above the deck 32 is also preferably made so as to form a single piece, and extends from its lower end 62 towards a second upper side end 64, the function of which is to be rigidly added onto the inner ribs of the fairing, as can be better seen in FIG. 4 showing a sectional view taken between two consecutive ribs.

This FIG. 4 shows that the heat protection deck 32 is added indirectly onto the lower portion 66 of the inner ribs 46 through two walls 58, that also form the only means of mounting the deck 32 on these ribs.

To achieve this, the second side end 64 of each of the two walls 58, that is at a distance from the deck 32 shifted downwards, is rigidly and directly fixed on the lower portion 66 of the inner ribs 46, in a position away from the side panels 44. Consequently, the deck 32 is no longer mounted directly on the inner ribs as was the case earlier, so that it can advantageously deform more freely due to thermal expansion as a result of the large amount of heat dissipated by the core engine flow 36 delimited by this deck 32.

In this respect, note that the heat protection deck 32 is provided with an outer surface reference 70 in FIG. 4, this surface being designed to delimit the core engine flow 36 that it partially delimits radially outwards, while the outer surfaces of side panels 44 are designed to delimit the fan flow 38.

In order to maintain an efficient separation between the core engine flow 36 circulating under the deck 32 and the fan flow 38 delimited by the side panels 44, in other words to prevent the very high temperature core engine flow from rising and propagating along these side panels 44, it is preferably arranged that, at any arbitrary cross-section of the fairing, the first end 62 of each longitudinal wall 58 together with its associated side deck end 60 jointly form a Y-shaped tip. More precisely, as shown, the Y is arranged such that its tip, namely its portion composed of the contact zone between the two ends 60, 62, faces approximately downwards and laterally outwards from the fairing 30, to correctly circumscribe the core engine flow 36 in the lower part of the fairing, namely along and in contact with the heat protection deck 32.

In this respect, and still in any arbitrary cross-section of the fairing, it can be seen that each longitudinal wall 58 is approximately in the shape of an inclined straight line so that the distance from a centre of the fairing reduces when moving towards its second side end 64, while the heat protection deck 32 located under these walls 58 is approximately in the form of a line forming a curve opening outwards from the fairing 30, still with the aim of circumscribing the core engine flow 36 in the lower part of this fairing.

Therefore, with this particular geometry, it is easy to arrange matters such that the entire deck is shifted and has no contact with the ribs 46, therefore a free space being provided between the lower portion 66 of the ribs and the deck 32.

Figure 5:
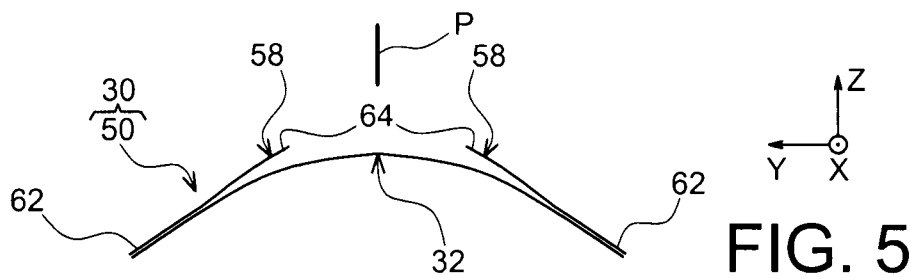
FIG. 5 shows a partial cross-sectional view taken along line V-V in FIG. 2.

Finally, note that the deck 32 which is rigidly and directly fixed at its two side ends 30 onto the two walls arranged symmetrically relative to the above-mentioned plane P, may have a curvature that gradually flattens out towards the aft direction, as can be understood from FIG. 5, corresponding to a cross-section taken further towards the aft direction and on which the deck 32 has a larger diameter curvature.

Considering that the heat protection deck 32 and the two longitudinal connection walls 58 do not have any direct rigid mechanical link with the side panels 44, and are preferably located lower than a lower end of these panels, the fairing 32 is preferably provided with additional means for making an aerodynamic junction between the lower end of each side panel 44 and its Y tip associated with it, facing it and a distance from it, formed by the side ends 60, 62 overlapping each other.

This is achieved by providing two aerodynamic extensions of the side panels 72, arranged symmetrically about plane P and each associated with one of the two side panels 44 that it prolongs in the direction of the heat protection deck 32, and more precisely in the direction of the Y formed jointly by the heat protection deck and by the associated longitudinal wall 58.

Preferably, each aerodynamic extension 72 is provided with a first or upper end 74 rigidly and directly fixed onto its associated side panel 44, and a second or lower end 76 cooperating with its associated deck side end 60, against which it is in bearing only. Preferably, the two links made at the two ends of each extension 72, namely the rigid link and the simple bearing link, extend continuously over the entire forward portion 50 of the fairing. In this respect, once again, each of the extensions 72 preferably extends in a single piece only along the forward portion 50 and not along the aft portion 52, although obviously this could be envisaged without going outside the framework of the invention. In general, it is noted that the aerodynamic extensions 72, the connection walls 58 and the heat protection deck 32 preferably extend over the same length along the X direction.

In any arbitrary cross-section of the fairing, each extension 72 is generally in the shape of an L, the base of which is composed of the lower end 76 in bearing with the tip of the Y formed by the ends in contact 60, 62 of the deck and the associated wall. Thus, it is preferably arranged that this lower end 76 should be in bearing contact with the deck 32 without being in contact with it directly, instead being in contact with the connection wall 58. Therefore, the required simple bearing link allowing free thermal expansion of the deck 32 is in the form of a surface contact extending along the entire forward portion 50 of the fairing.

Furthermore, the end of the long branch of the L that is oriented approximately along the Z direction forms the upper end 74 of the extension 72. It is rigidly fixed onto the lower end of the side panel 44 which may possibly extend slightly downwards beyond the inner ribs 46, as shown in FIG. 4, the attachment preferably being made by conventional rivet type means or similar means.

Finally, due to the particular design of the fairing 30 that has just been described in detail, all components of the fairing may be made from aluminum or from a composite material formed by a mix of resin and carbon and/or glass fibres, which advantageously reduces its mass and its manufacturing cost.

Obviously, those skilled in the art could make various modifications to the invention that has just been described through non-limitative examples. In this respect, note particularly that although the engine assembly 1 has been presented in a configuration appropriate for suspension under the aircraft wing, configuration of this assembly 1 could also be different such that it could be mounted above this wing.

The invention claimed is:

1. An aft pylon fairing for a suspension system for an engine, designed to be inserted between an aircraft wing and said engine, said fairing forming a box and comprising:
   two side panels assembled to each other by inner cross stiffening ribs spaced at intervals from each other along a longitudinal direction of said fairing;
   a heat protection deck provided with an outer surface designed to delimit a core engine flow of said engine, said heat protection deck having two opposite side ends; and
   two longitudinal connecting walls offsetting said heat protection deck from said inner cross stiffening ribs, each of said two longitudinal walls having a first side end fixed to one or the other of the two side ends of said heat protection deck, and a second side end rigidly fixed to said inner cross stiffening ribs.

2. The fairing according to claim 1, wherein in a cross-section of said fairing, said first end of each longitudinal wall and an associated side end of the heat protection deck work together to form a tip.

3. The fairing according to claim 1, wherein said heat protection deck is made so as to form a single piece.

4. The fairing according to claim 1, wherein each of the two longitudinal walls is made so as to form a single piece.

5. The fairing according to claim 1, wherein said second side end of each of the two longitudinal walls is mounted fixed on a lower portion of said inner stiffening cross ribs, at a distance from said side panels.

6. The fairing according to claim 1, wherein said heat protection deck and said two longitudinal walls do not have any rigid direct mechanical link with said side panels of the fairing.

7. The fairing according to claim 1, wherein said heat protection deck is offset from said inner cross ribs such that said heat protection deck has no contact with the ribs.

8. A suspension system for an engine designed to be inserted between an aircraft wing and said engine, the suspension system comprising:
   the aft pylon fairing according to claim 1.

9. An assembly comprising:
   an engine; and
   the suspension system for the engine according to claim 8.

10. An aircraft, comprising:
    at least the engine assembly according to claim 9.

* * * * *